US009546992B2

(12) United States Patent
Yamada et al.

(10) Patent No.: US 9,546,992 B2
(45) Date of Patent: Jan. 17, 2017

(54) FUEL PROPERTY JUDGMENT DEVICE AND METHOD OF JUDGING FUEL PROPERTY

(71) Applicant: DENSO CORPORATION, Kariya, Aichi-pref. (JP)

(72) Inventors: Naoyuki Yamada, Kariya (JP); Naoki Mikami, Takahama (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/723,793

(22) Filed: May 28, 2015

(65) Prior Publication Data
US 2015/0346180 A1    Dec. 3, 2015

(30) Foreign Application Priority Data

May 29, 2014    (JP) .................................. 2014-110801

(51) Int. Cl.
*G01N 33/00* (2006.01)
*G01N 33/28* (2006.01)
(Continued)

(52) U.S. Cl.
CPC ....... *G01N 33/2835* (2013.01); *F02D 41/1497* (2013.01); *F02D 41/28* (2013.01); *F02D 41/3809* (2013.01); *F02D 41/40* (2013.01); *F02D 2041/286* (2013.01); *F02D 2041/288* (2013.01); *F02D 2200/0602* (2013.01); *F02D 2200/0612* (2013.01); *F02D 2200/101* (2013.01)

(58) Field of Classification Search
CPC ............. G01N 33/2835; F02D 41/3809; F02D 41/1497; F02D 41/28; F02D 41/40; F02D 2041/288; F02D 2041/286; F02D 2200/0602; F02D 2200/0612; F02D 2200/101

See application file for complete search history.

(56) References Cited

U.S. PATENT DOCUMENTS

2009/0082940 A1    3/2009 Ishizuka et al.
2009/0198456 A1*   8/2009 Tsutsumi ............ F02D 41/0025
                                                702/41

(Continued)

FOREIGN PATENT DOCUMENTS

JP    2006-194224    7/2006
JP    2009-074499    4/2009
(Continued)

*Primary Examiner* — Hieu T Vo
*Assistant Examiner* — Sherman Manley
(74) *Attorney, Agent, or Firm* — Nixon & Vanderhye PC

(57) ABSTRACT

A fuel injection system has a common rail storing fuel, a fuel injector injecting the fuel, a fuel-passage supplying the fuel to the fuel injector, and a fuel-pressure sensor detecting a fuel pressure. An ECU acquires a waveform of a fuel pressure representing a change of a fuel pressure based on the detected fuel pressure at the fuel injection. The ECU calculates a speed of a fuel pressure wave forming the waveform of the fuel pressure based on a period of a pulsation of the waveform of the fuel pressure and a fuel passage length, and a fuel density based on the speed of the fuel pressure wave. The ECU further calculates a fuel cetane number, and a kinematic viscosity of the fuel based on the fuel density and the fuel cetane number. The ECU judges fuel properties based on the kinematic viscosity of the fuel.

16 Claims, 5 Drawing Sheets

(51) Int. Cl.
  *F02D 41/40* (2006.01)
  *F02D 41/14* (2006.01)
  *F02D 41/28* (2006.01)
  *F02D 41/38* (2006.01)

(56) References Cited

U.S. PATENT DOCUMENTS

| | | | | |
|---|---|---|---|---|
| 2009/0205413 | A1* | 8/2009 | Yamauchi | F02M 65/003 73/114.41 |
| 2010/0250095 | A1* | 9/2010 | Yamada | F02D 41/3809 701/103 |
| 2010/0312501 | A1* | 12/2010 | Komatsu | F02D 35/023 702/50 |
| 2010/0319443 | A1* | 12/2010 | Nakata | F02D 41/28 73/114.45 |
| 2010/0319445 | A1* | 12/2010 | Yamada | F02D 41/22 73/114.51 |
| 2011/0308497 | A1* | 12/2011 | Yamada | F02D 41/402 123/458 |
| 2013/0220006 | A1* | 8/2013 | Ito | F02D 41/0025 73/114.51 |
| 2013/0311063 | A1* | 11/2013 | Ito | F02D 41/1497 701/103 |

FOREIGN PATENT DOCUMENTS

| | | |
|---|---|---|
| JP | 2009-180174 | 8/2009 |
| JP | 2011-169332 | 9/2011 |
| JP | 2014-148906 | 8/2014 |

* cited by examiner

FUEL INJECTION INSTRUCTION SIGNAL

FUEL INJECTION RATE (LARGE)

FUEL PRESSURE (WAVEFORM OF FUEL PRESSURRE) (LARGE)

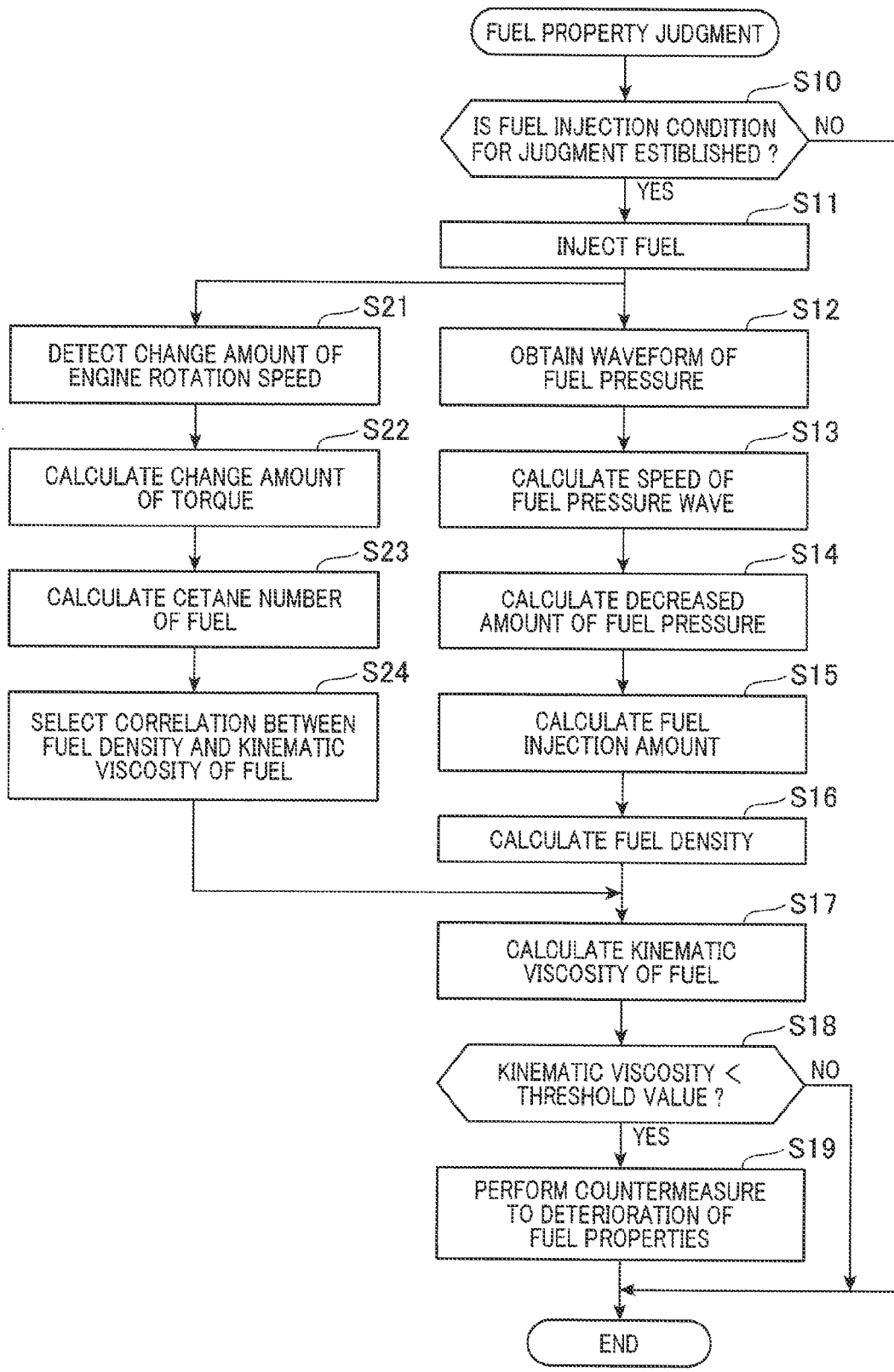

FUEL PROPERTY JUDGMENT DEVICE AND METHOD OF JUDGING FUEL PROPERTY

CROSS-REFERENCE TO RELATED APPLICATION

This application is related to and claims priority from Japanese Patent Application No. 2014-110801 filed on May 29, 2014, the contents of which are hereby incorporated by reference.

BACKGROUND OF THE INVENTION

1. Field of the Invention

The present invention relates to fuel property judgment devices and methods which judge properties of fuel to be supplied to a fuel injection system.

2. Description of the Related Art

There is a conventional device capable of judging occurrence of abnormality of a fuel supply pump when a temperature of fuel flowing in the inside of the fuel supply pump exceeds a predetermined temperature. For example, a patent document 1, Japanese patent laid open publication No. 2006-194224 has disclosed such a conventional judgment device. When abnormality such as a fuel flow failure occurs in the inside of the fuel flow pump by using an inferior fuel, for example, because a temperature of the fuel as a lubricant oil increases, the device judges occurrence of abnormality of the fuel supply pump on the basis of the detected increased temperature of the fuel.

However, because a temperature of fuel gradually increases and it takes a long time before the device correctly detects the occurrence of abnormality of the fuel supply pump, there is a possible impediment to the motion of the fuel supply pump and fuel injectors, etc. That is, it is necessary for the device to use a high precision temperature sensor in order to detect a temperature of fuel with quick responsiveness and high accuracy.

SUMMARY

It is therefore desired to provide a fuel property judgment device and a method of detecting properties of fuel with quick responsiveness and high accuracy.

An exemplary embodiment provides a fuel property judgment device for use in a fuel injection system. The fuel injection system has a pressure accumulation chamber such as a common rail, one or more fuel injectors, a fuel passage and a fuel passage sensor. The pressure accumulation chamber is capable of storing high pressure fuel. Each of the fuel injectors has a fuel injection hole through which the fuel is injected into a corresponding cylinder of an internal combustion engine such as a diesel engine. Through the fuel passage the fuel is supplied from the pressure accumulation chamber to the fuel injection hole. The fuel pressure sensor is capable of detecting a fuel pressure of the fuel in the fuel passage. The fuel property judgment device has a fuel pressure waveform acquiring section, a fuel pressure wave speed calculation section, a fuel density calculation section, a fuel cetane number calculation section, a fuel kinematic viscosity calculation section and a judgment section. The fuel pressure waveform acquiring section acquires a waveform of a fuel pressure which represents a change of a fuel pressure of the fuel on the basis of the fuel pressure detected by the fuel pressure sensor when the fuel injector injects the fuel. The fuel pressure wave speed calculation section calculates a speed of a fuel pressure wave which forms the waveform of the fuel pressure on the basis of a period of a pulsation of the waveform of the fuel pressure obtained by the fuel pressure waveform acquiring section and a fuel passage length. The fuel density calculation section calculates a density of the fuel on the basis of the speed of a fuel pressure wave calculated by the fuel pressure wave speed calculation section. The fuel cetane number calculation section calculates a cetane number of the fuel. The fuel kinematic viscosity calculation section calculates a kinematic viscosity of the fuel on the basis of the density of the fuel calculated by the fuel density calculation section and the cetane number of the fuel calculated by the fuel cetane number calculation section. The judgment section judges a state of fuel properties of the fuel on the basis of the kinematic viscosity of the fuel calculated by the fuel kinematic viscosity calculation section.

In the fuel property judgment device having the structure previously described, the pressure accumulation chamber such as a common rail stores high pressure fuel. The high pressure fuel is supplied from the pressure accumulation chamber to the fuel injection hole of the fuel injector. The fuel passage sensor detects a fuel pressure of the fuel flowing in the fuel passage. In addition, a cetane number of the fuel is also calculated. There are various methods to calculate the cetane number of the fuel.

A waveform of a fuel pressure, which represents a change of a fuel pressure of the fuel, is calculated on the basis of the fuel pressure detected by the fuel pressure sensor when the fuel injector injects the fuel. A speed of a fuel pressure wave forming the waveform of the fuel pressure is calculated on the basis of a period of a pulsation of the calculated waveform of the fuel pressure and the fuel passage length. That is, the fuel pressure wave remained in the fuel passage moves in a reciprocating motion in the inside of the fuel passage after the fuel injection. It is therefore possible to calculate a speed of the fuel pressure wave on the basis of the period of a pulsation of the waveform of the fuel pressure wave and the fuel passage length. In view of the pulsation of the waveform of the fuel pressure wave, it is acceptable to arrange the fuel pressure sensor at an optional location in the fuel passage. The density of the fuel is calculated on the basis of the calculated speed of the fuel pressure wave. That is, it is possible to calculate the density of the fuel on the basis of the physical relationship between the speed of the fuel pressure wave and the density of the fuel.

The kinematic viscosity of the fuel is calculated on the basis of the calculated density of the fuel and the calculated cetane number of the fuel. That is, there is a correlation between the fuel density and the kinematic viscosity of the fuel. It is possible to have a strong correlation between the density of the fuel and the kinematic viscosity of the fuel by further considering the cetane number of the fuel. It is therefore possible to calculate the kinematic viscosity of the fuel on the basis of the density of the fuel by using the correlation previously described. It is possible to obtain the correlation between the density of the fuel, the kinematic viscosity of the fuel, and the cetane number of the fuel in advance on the basis of results of various experiments.

Because the kinematic viscosity of the fuel represents the characteristics of the fuel as a lubricant, it is possible to judge whether or not the fuel has correct fuel properties on the basis of the kinematic viscosity of the fuel. It is possible to judge the fuel conditions on the basis of the fuel pressure detected by the fuel pressure sensor at the timing of the fuel injection. Accordingly, this makes it possible for the fuel property judgment section to quickly judge whether or not the fuel has correct fuel properties with high accuracy.

In accordance with another aspect of the present invention, there is provided a fuel property judgment device for use in a fuel injection system. The fuel injection system has a pressure accumulation chamber such as a common rail, one or more fuel injectors, a fuel passage and a fuel passage sensor. The pressure accumulation chamber stores high pressure fuel. Each of the fuel injectors has a fuel injection hole through which the fuel is injected into a corresponding cylinder of an internal combustion engine such as a diesel engine. Through the fuel passage the fuel is supplied from the pressure accumulation chamber to the fuel injection hole. The fuel pressure sensor detects a fuel pressure of the fuel in the fuel passage. The fuel property judgment device has a fuel pressure waveform acquiring section, a fuel pressure wave speed calculation section, a fuel density calculation section, a fuel cetane number calculation section, and a judgment section. The fuel pressure waveform acquiring section acquires a waveform of a fuel pressure which represents a change of a fuel pressure of the fuel on the basis of the fuel pressure detected by the fuel pressure sensor when the fuel injector injects the fuel. The fuel pressure wave speed calculation section calculates a speed of a fuel pressure wave which forms the waveform of the fuel pressure on the basis of a period of a pulsation of the waveform of the fuel pressure obtained by the fuel pressure waveform acquiring section and a fuel passage length of the fuel passage. The fuel density calculation section calculates a density of the fuel on the basis of the speed of a fuel pressure wave calculated by the fuel pressure wave speed calculation section. The fuel cetane number calculation section calculates a cetane number of the fuel.

The judgment section judges a state of fuel properties of the fuel on the basis of the density of the fuel calculated by the fuel density calculation section and the cetane number of the fuel calculated by the fuel cetane number calculation section.

As previously described, there is a correlation between the density of the fuel, the kinematic viscosity of the fuel, and the cetane number of the fuel. Accordingly, it is possible to judge the fuel properties of the fuel on the basis of the calculated density of the fuel and the calculated cetane number of the fuel with high accuracy.

In accordance with another aspect of the present invention, there is provided a method of judging fuel properties to be used in a fuel injection system. The fuel injection system has the structure previously described. In particular, the method has at least the following steps. An acquiring step acquires a waveform of a fuel pressure which represents a change of a fuel pressure of the fuel on the basis of the fuel pressure detected when the fuel injector injects the fuel. A speed calculating step calculates a speed of a fuel pressure wave which forms the waveform of the fuel pressure on the basis of a period of a pulsation of the waveform of the fuel pressure and a fuel passage length of the fuel passage. A density calculating step calculates a density of the fuel on the basis of the speed of the calculated fuel pressure wave. A cetane number calculating step calculates a cetane number of the fuel. A kinematic viscosity calculating step calculates a kinematic viscosity of the fuel on the basis of the calculated density of the fuel and the calculated cetane number of the fuel. A judging step judges a state of fuel properties of the fuel on the basis of the calculated kinematic viscosity of the fuel.

It is possible for the method to provide the same action and effects of the fuel property judgment device previously described.

BRIEF DESCRIPTION OF THE DRAWINGS

A preferred, non-limiting embodiment of the present invention will be described by way of example with reference to the accompanying drawings, in which:

FIG. 3 is a flow chart showing a fuel property judgment process performed by the fuel property judgment device in the fuel injection system shown in FIG. 1;

DETAILED DESCRIPTION OF THE PREFERRED EMBODIMENTS

Figure 1:
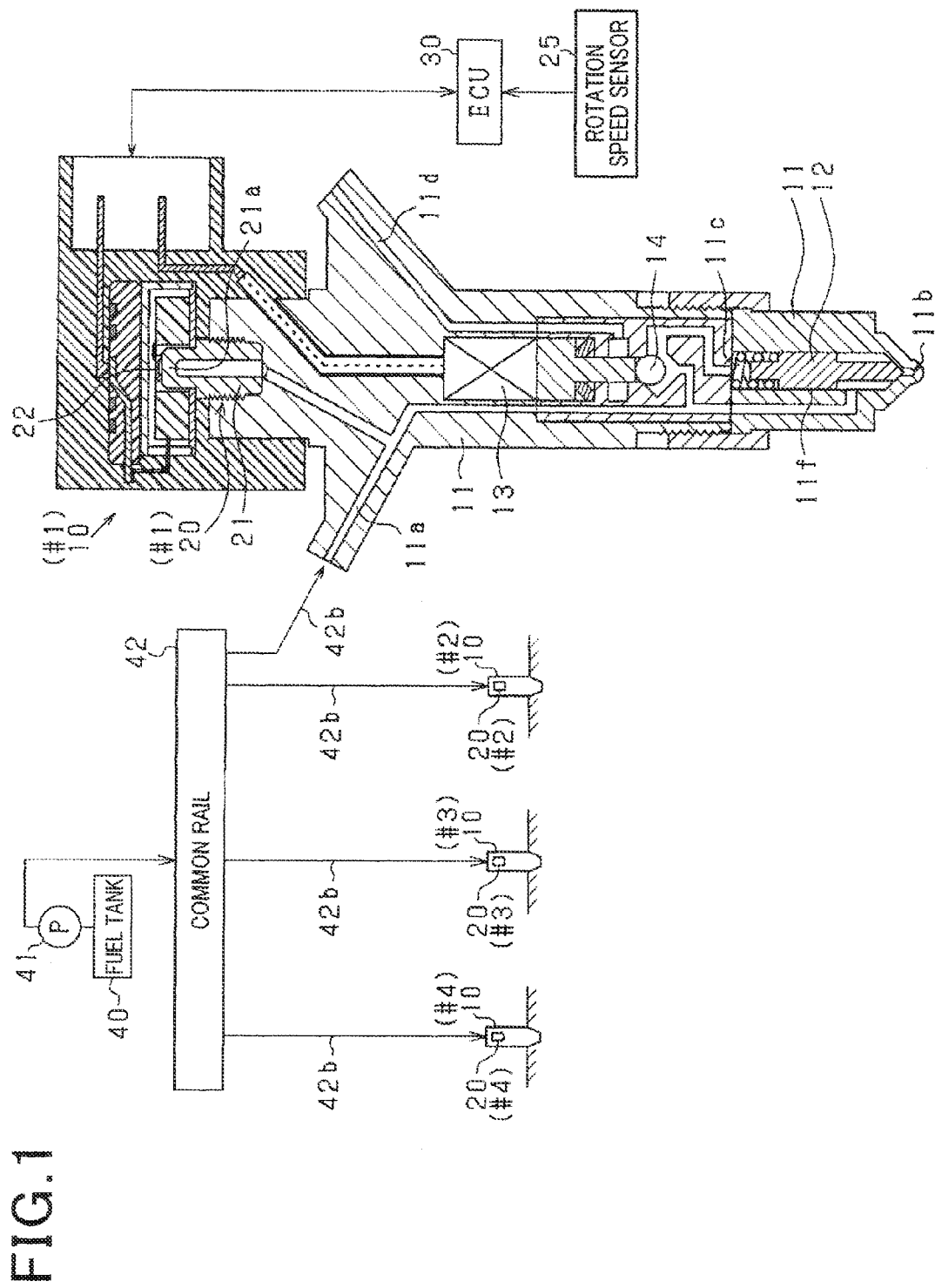
FIG. 1 is a schematic view showing a fuel injection system having a fuel property judgment device according to an exemplary embodiment of the present invention.

Hereinafter, various embodiments of the present invention will be described with reference to the accompanying drawings. In the following description of the various embodiments, like reference characters or numerals designate like or equivalent component parts throughout the several diagrams.

Exemplary Embodiment

A description will be given of a fuel property judgment device and a method according to an exemplary embodiment with reference to FIG. 1 to FIG. 6. The fuel property judgment device according to the exemplary embodiment is applied to a fuel injection system of a common rail type for a diesel engine mounted on a motor vehicle.

FIG. 1 is a schematic view showing the fuel injection system having the fuel property judgment device according to the exemplary embodiment. The exemplary embodiment uses a diesel engine (internal combustion engine) having four cylinders #1 to #4. As shown in FIG. 1, fuel injectors 10 inject a high pressure fuel into the cylinders #1 to #4 of the diesel engine in order to perform compression ignition combustion in the cylinders #1 to #4 of the diesel engine.

That is, FIG. 1 shows a schematic structure of the fuel injection system having the fuel injectors 10 and the fuel property judgment device according to the exemplary embodiment. A description will now be given of the fuel injection system for the diesel engine having the fuel injectors 10.

A fuel tank 40 stores fuel. A fuel pump 41 supplies high pressure fuel to a common rail 42 (pressure accumulation chamber). The common rail 42 stores the high pressure fuel. The common rail 42 communicates with the fuel injectors 10 (which correspond to the cylinders #1 to #4 of the diesel engine, respectively) through fuel pipes 42b. The high pressure fuel stored in the common rail 42 is supplied to the fuel injectors 10 (corresponding to the cylinders #1 to #4, respectively). The fuel injectors 10 inject the fuel injection in a predetermined order. The exemplary embodiment performs the fuel injection repeatedly in the order of the fuel injection value #1, the fuel injection value #3, the fuel injection value #4, and the fuel injection value #2.

The fuel pump 41 is equipped with a plunger pump having a plunger so that the high pressure fuel is supplied in synchronization with a plunger's reciprocating motion. The fuel pump 41 is driven by a crank shaft of the diesel engine as a drive power source. The fuel pump 41 supplies the high pressure fuel to the cylinder #1, the cylinder #3, the cylinder #4, and the cylinder #2, in order during the fuel injection period predetermined times.

Each of the fuel injectors 10 is equipped with a body 11, a needle valve 12, and an electric actuator 13, etc. The body 11 has a high pressure fuel passage 11a therein and an injection hole through which the fuel is injected into the corresponding cylinder. The body 11 accommodates the needle valve 12 in order to open and close a fuel injection hole 11b. The fuel pipes 42b and the high pressure fuel passage 11a form a fuel passage through which high pressure fuel is supplied from the common rail 42 to the injection hole 11b of each of the fuel injectors 10.

A back pressure chamber 11c is formed in the inside of the body 11 to supply a back pressure to the needle valve 12. A high pressure passage 11a and a low pressure passage 11d communicate with the back pressure chamber 11c. The electric actuator 13 drives a control valve 14 to switch a connection of the back pressure chamber 11c to the high pressure fuel passage 11a or the low pressure passage 11d. An engine control unit (ECU) 30 controls the operation of the electric actuator 13.

When the ECU 30 operates the control valve 14 to communicate the back pressure chamber 11c to the low pressure passage 11d, a pressure of the fuel stored in the back pressure chamber 11c decreases, and the needle valve 12 is lifted up (valve-open), and the injection hole 11b opens. As a result, the high pressure fuel, supplied from the common rail 42 to the high pressure passage 11a is injected into the combustion chamber through the injection hole 11b.

On the other hand, when the ECU 30 operates the control valve 14 to communicate the back pressure chamber 11c with the high pressure fuel passage 11a, the pressure of the fuel in the back pressure chamber 11c increases, and the needle valve 12 drops down (valve-close), and the injection hole 11 is closed. The fuel injection is stopped.

A fuel pressure sensor 20 is equipped with a stem 21, a pressure sensor element 22, etc. The stem 21 is attached to the body 11. A diaphragm section 21a is formed in the stem 21. The diaphragm section 21a is elastically deformed by the pressure of the high pressure fuel passing through the high pressure fuel passage 11a. A pressure sensor element 22 is attached to the diaphragm section 21a. The diaphragm section 21a generates a pressure detection signal due to an amount of elastic deformation generated in the diaphragm section 21a. The pressure sensor element 22 transmits the generated pressure detection signal to the ECU 30.

The fuel pressure sensor 20 is mounted to each of the fuel injectors 10. Hereinafter, the fuel injector 10 mounted to the cylinder #1 will be referred to as the "injector 10 (#1), and the fuel pressure sensor 20 mounted to the injector 10 (#1) will be referred to as the "fuel pressure sensor 20 (#1)". Likewise, the fuel injectors 10 mounted to the cylinders #2 to #4 will be referred to as the "injectors 10 (#1) to (#4), respectively. The fuel pressure sensors 20 mounted to the injectors 10 (#2) to (#4) will be referred to as the "fuel pressure sensors 20 (#1) to (#4)", respectively.

The ECU 30 is a microcomputer having a known structure, which is available on the commercial market. That is, the ECU 30 is equipped with a central processing unit (CPU), a read only memory (ROM), a random access memory (RAM), a memory device and an input/output interface, etc.

The ECU 30 calculates injection target conditions on the basis of an operation amount of an acceleration pedal, an engine load amount, an engine rotation speed NE, etc. of a motor vehicle. For example, the ECU 30 makes a map regarding optimum injection conditions corresponding to an engine load amount and an engine rotation speed, and stores the map into the memory section. The ECU 30 fetches the data from the map on the basis of a current engine load amount and a current engine rotation speed, and calculates optimum injection target conditions on the basis of the fetched data.

Figure 2A:
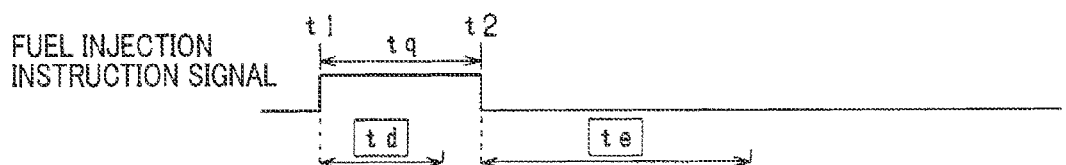
FIG. 2A to FIG. 2C are timing charts showing a change of an fuel injection rate and a fuel pressure corresponding to fuel injection instruction signals used by the fuel injection system shown in FIG. 1.
Figure 2B:
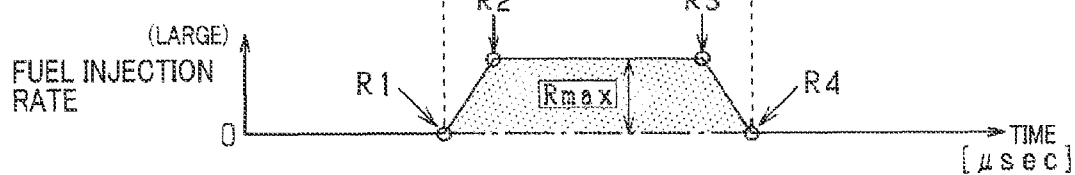
Figure 2C:
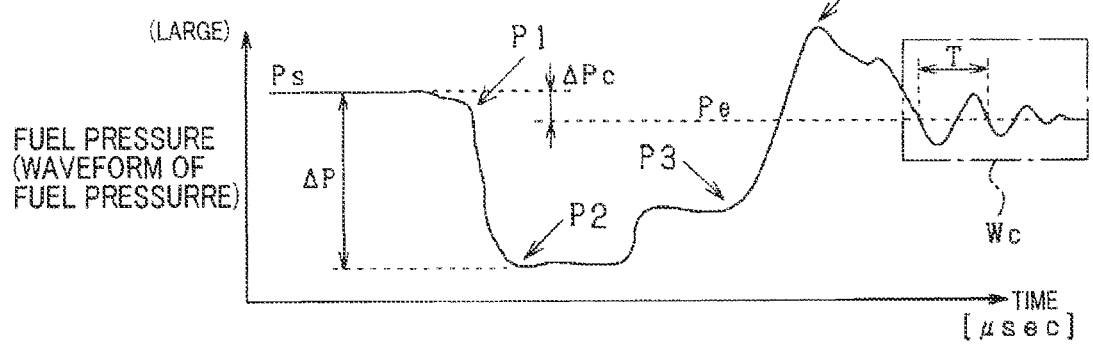

FIG. 2A to FIG. 2C are timing charts showing a change of an fuel injection rate and a fuel pressure corresponding to fuel injection instruction signals used by the fuel injection system shown in FIG. 1.

As shown in FIG. 2A, the ECU 30 generates the fuel injection instruction signals t1, t2 and tq which correspond to the calculated optimum injection target conditions on the basis of fuel injection rate parameters td, te and Rmax. The ECU 30 calculates learned values regarding to the fuel injection rate parameters td, te and Rmax on the basis of a change of detection values (a waveform of the fuel pressure) transmitted from the fuel pressure sensors 20. These fuel injection rate parameters td, te and Rmax will be explained in detail later.

Next, a description will now be given of a method of obtaining these fuel injection rate parameters and calculating the learned values regarding the fuel injection rate parameters with reference to FIG. 2A to FIG. 2C. The following description explanation will explain the learned values of the fuel injection rate parameters on the basis of the detection values transmitted from the fuel pressure sensor 20 (#1) only. However, the other learned values can be obtained on the basis of the detection values transmitted from the other fuel pressure sensors 20 (#2) to (#4) by the same method. That is, the ECU 30 calculates the learned values of the fuel injection rate parameters on the basis of the detection values transmitted from the fuel pressure sensors 20 (#1) to (#4).

For example, when the injector 10 (#1) injects fuel into the corresponding cylinder #1, the ECU 30 detects a waveform of a fuel pressure (see FIG. 2C), as a change of the fuel pressure caused by the fuel injection, on the basis of the detection values transmitted from the fuel pressure sensor 20 (#1). The ECU 30 calculates a waveform of the fuel injection rate (see FIG. 2B) on the basis of the waveform of the detected fuel pressure, which indicates a change of the fuel injection amount per unit time. The ECU 30 calculates the learned values of the fuel injection rate parameters td, te and Rmax which specify the waveform of the fuel injection rate (as fuel injection state), and performs the fuel injection control on the basis of the learned values of the fuel injection rate parameters td, te and Rmax.

As shown in FIG. 2C, the detection value of the fuel pressure transmitted from the fuel pressure sensor 20 (#1) decreases at the change point P due to the start of the fuel injection, reaches the maximum fuel injection rate, and then decreases, and has the minimum value at the change point P2. After the change point P2, the detection value of the fuel pressure transmitted from the fuel pressure sensor 20 (#1) starts to increase at the change point P3 caused when the needle valve 12 starts to drop down (valve-close). After this, the detection value of the fuel pressure transmitted from the fuel pressure sensor 20 (#1) completes to increase at the change point P4 when the needle valve 12 is closed and the fuel injection stops. After this, the detection value of the fuel pressure transmitted from the fuel pressure sensor 20 (#1) gradually attenuates with a pulsation while repeatedly increasing and decreasing (as designated by the long dashed short dashed line We in FIG. 2C). That is, after the fuel injection, a stationary wave is generated in the fuel pipe 42b and the high pressure fuel passage 11a by a reciprocating motion of the waveform of the fuel pressure of the fuel remained in the fuel pipe 42b and the high pressure fuel passage 11a.

Immediately after the fuel injection, a fuel pressure of the fuel in the overall system is decreased by a fuel injection amount. In more detail, as shown in FIG. 3C, the fuel pressure of the fuel is reduced from a reference pressure Ps before the fuel injection to the fuel pressure Pe immediately after the fuel injection by a decreased fuel amount ΔPc.

The waveform of the fuel pressure shown in FIG. 2C and the fuel injection rate shown in FIG. 2B correlate to each other. Specifically, there is a correlation between the generation timing of the sudden change point P1 (see FIG. 2C) and the fuel injection start timing R1 (see FIG. 2B). Similarly, there is a correlation between the generation timing of the change point P3 (see FIG. 2C) and the fuel injection completion timing R4 (see FIG. 2B). Further, there is a correlation between a fuel pressure drop amount ΔP from the sudden change point P1 to a change point P2 and the maximum fuel injection rate (the fuel injection rate parameter Rmax).

FIG. 2A shows the fuel injection instruction signals transmitted to the fuel injector 10 (#1). The fuel injection rate parameter td, previously described, represents a delay time (fuel injection start delay time td) of the fuel injection start timing R1 from a fuel injection start instruction timing t1.

The fuel injection rate parameter te represents a delay time (fuel injection completion delay time te) of the fuel injection completion timing R4 from a fuel injection completion instruction timing t2.

Accordingly, variable correlation coefficients representing the variable correlations previously described are obtained in advance. The ECU 30 calculates the fuel injection rate parameters td, te and Rmax on the basis of the generation timings of the change points P3 and P4 and the fuel pressure drop amount ΔP obtained from the waveform of the fuel pressure of the fuel pressure sensor 20 (#1) by using these correlation coefficients.

In addition, the ECU 30 can estimate a waveform of the fuel injection rate on the basis of these fuel injection rate parameters td, te and Rmax. The ECU 30 calculates the fuel injection amount Q of the fuel injector 10 (#1) on the basis of an area of the estimated waveform of the fuel injection rate (designated by the hatched area (or dotted area) in FIG. 2B).

As previously described, it is possible for the ECU 30 to calculate an actual fuel injection state corresponding to the fuel injection instruction signals on the basis of the detection values transmitted from the fuel pressure sensor 20 (#1), and obtain the learned values on the basis of the calculated actual fuel injection state. The ECU 30 calculates the target fuel injection state on the basis of the obtained learned values, and generates the fuel injection instruction signals on the target fuel injection state.

A description will now be given of the fuel property judgment process performed by the ECU 30 as the fuel property judgment device in the fuel injection system. The fuel property judgment process judges properties of currently-used fuel.

FIG. 3 is a flow chart showing the fuel property judgment process performed by the ECU 30 as the fuel property judgment device in the fuel injection system shown in FIG. 1.

The ECU 30 (fuel property judgment device) repeatedly performs the fuel property judgment process at a predetermined period.

In step S10 shown in FIG. 3, the ECU 30 judges whether or not a predetermined condition is established in order to correctly perform the fuel injection of the fuel property judgment. Specifically, when a warming-up operation of the diesel engine has been completed and the diesel engine is in a fuel-cut condition, the ECU 30 judges that the predetermined condition for the fuel injection of the fuel property judgment has been established.

When the judgment result in step S10 indicates negation ("NO" in step S10), the operation flow goes to the END step. The ECU 30 completes the fuel property judgment process shown in FIG. 3.

On the other hand, when the judgment result in step S10 indicates affirmation ("YES" in step S10), i.e. indicates that the predetermined condition of the fuel injection of the fuel property judgment has been established, the operation flow goes to step S11.

In step S11, the fuel injector injects fuel into the corresponding cylinder. In more detail, when the engine rotation speed NE reaches a predetermined engine rotation speed NEj, the ECU 30 generates and transmits the fuel injection instruction signal to one of the fuel injectors 10 in order to inject fuel of a predetermined amount Qj. This fuel injection during the fuel property detection process is performed for one of the fuel injection values 10 once only. At this time, the ECU 30 transmits the fuel injection signal to the fuel injector 10 so that the fuel injector 10 injects fuel of the predetermined amount Qj.

The ECU 30 performs the process in the steps S12 to S16 to calculate a fuel density ρ and the process in the steps S21 to S24 to select a correlation between the fuel density ρ and a kinematic viscosity ν, simultaneously. It is acceptable for the ECU 30 to perform the process in steps S12 to S16 and the process in step S21 to S24 at different timings. The operation goes to step S12.

In step S12, the ECU 30 obtains the waveform of the fuel pressure (see FIG. 2C) as the fuel pressure change caused by the fuel injection on the basis of the detection value of the fuel pressure sensor 20 (#1) when the fuel injector 10 (#1) injects fuel, for example. The operation flow goes to step S13.

In step S13, the ECU 30 calculates the speed v of the fuel pressure wave which forms the waveform of the fuel pressure. In more detail, as shown by the long dashed short dashed line We in FIG. 2C, the ECU 30 measures one period of the pulsation in the waveform of the fuel pressure generated after the fuel injection, and calculates a period T of the pulsation of the waveform of the fuel pressure.

The ECU 30 divides the length 2L which is twice of the fuel passage length L which is a sum of the of the fuel passage length of the fuel pipe 42b and the fuel passage length of the high pressure fuel passage 11a by the period T in order to obtain the speed v of the fuel pressure wave. The operation flow goes to step S14.

In step S14, the ECU 30 calculates a decreased fuel amount ΔPc of the fuel pressure before and after the fuel injection of the fuel injector 10 (#1). In more detail as shown in FIG. 2C, the ECU 30 subtracts the fuel pressure Pe after the fuel injection from the reference fuel pressure Ps before the fuel injection to obtain the fuel decrease amount ΔPc (i.e., ΔPc=Ps−Pe). The operation flow goes to step S15.

In step S15, the ECU 30 calculates the fuel injection amount Q of the fuel injected by the fuel injector 10 (#1). In more detail, as previously described, the ECU 30 estimates the waveform of the fuel injection rate on the basis of the fuel injection rate parameters td, to and Rmax, and calculates the fuel injection amount Q on the basis of the area (see the hatched area (or dotted area) in FIG. 2B) of the waveform of the estimated fuel injection rate. It is possible to optionally change the order to execute the step S13 to S15. The operation flow goes to step S16.

In step S16, the ECU 30 calculates the fuel density ρ on the basis of the speed v of the fuel pressure wave, the decreased fuel amount ΔPc, the fuel injection amount Q, and the volume V of the fuel passage. In more detail, the ECU 30 calculates the fuel density ρ by using the following equation regarding fluid mechanics:

$$\rho = \Delta Pc \times V/(Q \times v^2),$$

where the volume V is a sum of the volume of the fuel pipes 42b and the volume of the high pressure fuel passage 11a.

The ECU 30 also performs the process in step S21. In step S21, the ECU 30 calculates a change amount ΔNE of the engine rotation speed NE after the fuel injection of the fuel injector 10 (#1).

Figure 4:
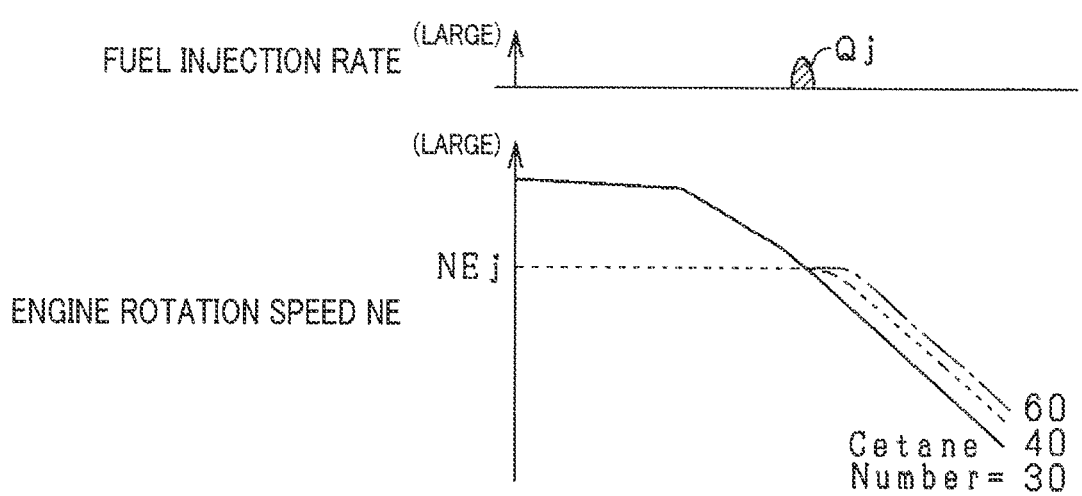
FIG. 4 is a graph showing a relationship between a cetane number and an engine rotation speed when the fuel injectors inject fuel during a fuel property judgment performed by the fuel property judgment device according to the exemplary embodiment of the present invention.

FIG. 4 is a graph showing a relationship between a cetane number and the engine rotation speed NE when the fuel injectors 10 (#1, #2, #3, and #4) inject fuel during a fuel property judgment performed by the ECU 30 as the fuel property judgment device according to the exemplary embodiment.

As shown in FIG. 4, when the fuel injector 10 (#1) injects the fuel of the predetermined amount Qj at the timing when the engine rotation speed NE reaches the predetermined engine rotation speed NEj, the engine rotation speed NE increases due to the torque Tq generated by the combustion of the injected fuel. Accordingly, the ECU 30 detects the change amount ΔNE of the engine rotation speed NE caused by the fuel injection on the basis of the engine rotation speed NE detected by an engine rotation speed sensor 25. The operation flow goes to step S22.

In step S22, the ECU 30 calculates a change amount ΔTq of the torque Tq on the basis of the detected change amount ΔNE. In more detail, the ECU 30 calculates the torque Tq of the diesel engine by using the following equation.

$$Tq = k \times NE \times \Delta NE,$$

where k is a proportional constant.

The ECU 30 calculates the change amount ΔTq of the torque Tq of the diesel engine.

As shown in FIG. 4, when the fuel injector 10 (#1) injects the fuel of the predetermined amount Qj, an increased amount of the engine rotation speed NE varies depending on the cetane number CN of the fuel. Specifically, the more the cetane number of fuel increases, the more the increased amount of the engine rotation speed NE increases. Accordingly, the change amount ΔTq of the torque Tq of the diesel engine calculated on the basis of the engine rotation speed Ne varies due to the cetane number of the fuel. The operation flow goes to step S13.

In step S23, the ECU 30 calculates the cetane number of the fuel on the basis of the change amount ΔTq of the torque Tq of the diesel engine. In more detail, the ECU 30 calculates the cetane number of the fuel on the basis of a relationship between the cetane number of the fuel and the change amount ΔTq of the torque Tq of the diesel engine, where the change amount ΔTq of the torque Tq of the diesel engine is obtained in advance by experiments.

It is also possible for the ECU 30 to calculate the cetane number of the fuel on the basis of the change amount ΔNE of the engine rotation speed NE caused by the fuel injection. The operation flow goes to step S24.

Figure 5:
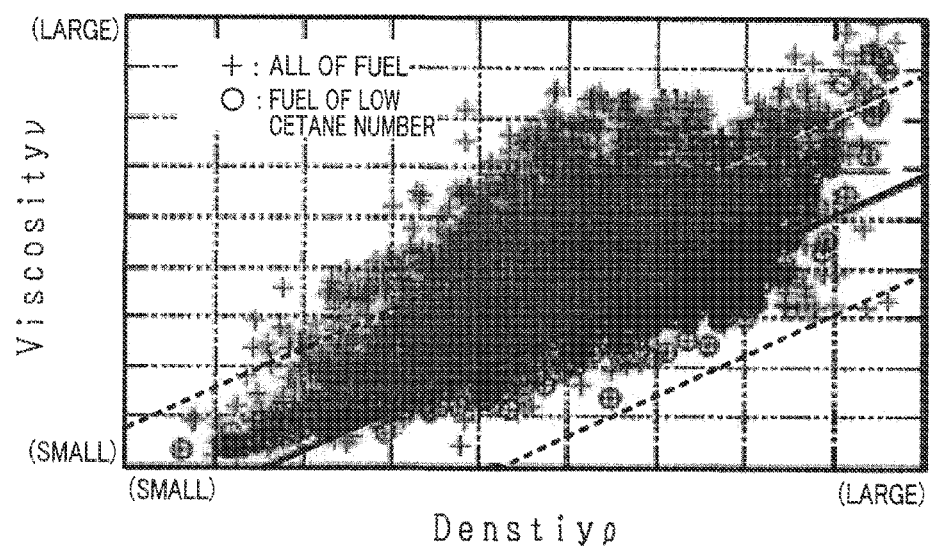
FIG. 5 is a graph showing a correlation between a density of low cetane number fuel and kinematic viscosity.

FIG. 5 is a graph showing a correlation between a fuel density ρ of a low cetane number fuel and a kinematic viscosity v.

In step S24, the ECU 30 selects a correlation between the fuel density ρ and the kinematic viscosity v on the basis of the calculated cetane number. In more detail, as shown in FIG. 5, there is in general a correlation between the fuel density ρ and the kinematic viscosity v of fuel. However, different fuels have a different correlation between the fuel density ρ and the kinematic viscosity v. Fuel of a low cetane number, as designated by reference character "O", has a strong correlation between the fuel density ρ and the kinematic viscosity v with only a small variation.

The solid line shown in FIG. 5 indicates a graph showing the correlation between the fuel density ρ and the kinematic viscosity v in a low cetane number fuel. The dashed straight lines shown in FIG. 5 show an upper limit and a lower limit of a range in which a variation measured from the solid line becomes small rather than a predetermined value.

Figure 6:
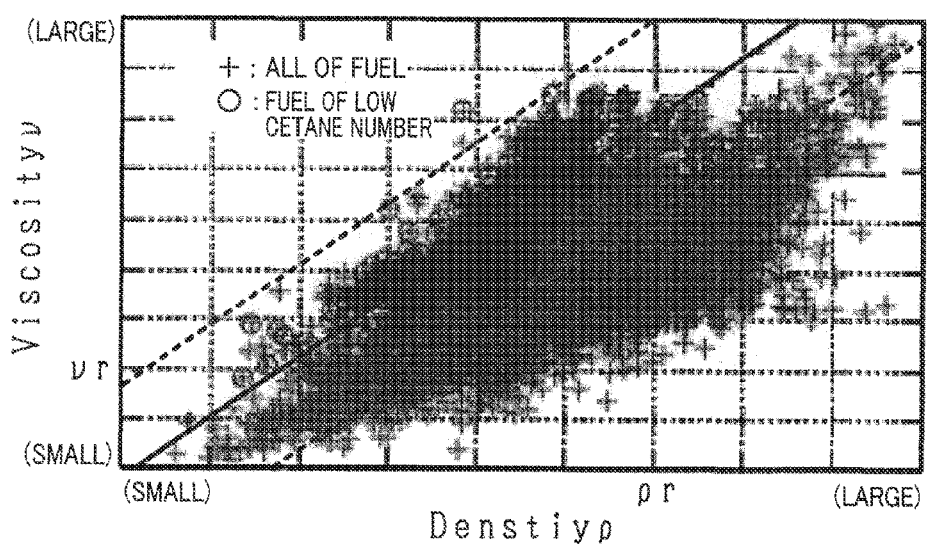
FIG. 6 is a graph showing a correlation between a density of high cetane number fuel and kinematic viscosity.

FIG. 6 is a graph showing a correlation between a fuel density ρ of high cetane number fuel and a kinematic viscosity.

As designated by reference character "O" shown in FIG. 6, the high cetane number fuel has a strong correlation between the fuel density ρ and the kinematic viscosity v and has a relatively small variation.

As compared with the low cetane number fuel shown in FIG. 5, the high cetane number fuel is shifted toward a higher kinematic viscosity v side and an increased slope, as designated by the solid line shown in FIG. 6. The ECU 30 selects an optimum graph showing the correlation between the fuel density ρ and the kinematic viscosity v in a low cetane number fuel on the basis of the calculated cetane number of fuel.

In step S17, the ECU 30 calculates the kinematic viscosity v of the fuel on the basis of the fuel density ρ by using the graph which shows the correlation between the fuel density ρ and the kinematic viscosity v of the selected fuel. That is, the ECU 30 calculates the kinematic viscosity v of the fuel on the basis of the calculated fuel density ρ by using the correlation between the fuel density ρ and the kinematic viscosity v, and the cetane number of the fuel. The operation flow goes to step S18.

In step S18, the ECU 30 judges whether or not the calculated kinematic viscosity v of the fuel is smaller than a threshold value γ. The more the kinematic viscosity v of fuel has a low value, the more the lubricant property of fuel is reduced, and the fuel has a low lubricant property. The threshold value γ is determined to determine whether or not fuel to be used provides negative influence.

When the judgment result in step S18 indicates affirmation ("YES" in step S18), i.e. that the calculated kinematic viscosity v of the fuel is smaller than the threshold value γ, the operation flow goes to step S19.

In step S19, the ECU 30 performs countermeasure to deterioration of the fuel properties of the fuel.

The fuel injection characteristics of the fuel injectors 10 change due to the kinematic viscosity v of the fuel. Accordingly, the ECU 30 controls the fuel injection state of the fuel injectors 10 on the basis of the calculated kinematic viscosity ν of the fuel. In more detail, the ECU 30 adjusts, i.e. compensates the target fuel injection state (fuel injection steps, the fuel injection start timing, the fuel injection completion timing, fuel injection amount, etc.) The ECU 30 completes the process shown in FIG. 3.

On the other hand, when the judgment result in step S18 indicates negation ("NO" in step S18), i.e. that the calculated kinematic viscosity ν of the fuel is not smaller than the threshold value γ, The ECU 30 completes the process shown in FIG. 3. That is, the ECU 30 judges that the fuel has correct properties, and performs no countermeasure to deterioration of the fuel property of the fuel.

The process in step S12 corresponds to a fuel pressure waveform acquiring section, and the process in step S13 corresponds to a fuel pressure wave speed calculation section. The process in step S14 corresponds to a decrease amount calculation section, and the process in step S15 corresponds to a fuel injection amount calculation section. The process in step S21 to step S23 correspond to a fuel cetane number calculation section, and the process in step S17 corresponds to a fuel kinematic viscosity calculation section. The process in step S18 corresponds to a judgment section, and the process in step S19 corresponds to a control section.

The fuel property judgment device according to the exemplary embodiment previously described has the following features and effects.

The ECU 30 calculates the waveform of the fuel pressure on the basis of the fuel pressure detected by the fuel pressure sensor 20 when the fuel injectors 10 inject fuel. The waveform of the fuel pressure indicates a change of the fuel pressure.

The ECU 30 calculates a speed v of a fuel pressure wave which forms a waveform of the fuel pressure on the basis of the period T of the pulsation of the waveform of the fuel pressure and the fuel passage length L. That is, the fuel pressure wave, which remains in the inside of the fuel passage after the fuel injection, reciprocates in the fuel passage and generates a pulsation. Accordingly, it is possible for the ECU 30 to calculate the speed v of the fuel pressure wave on the basis of the period T of the pulsation of the waveform of the fuel pressure and the fuel passage length L.

It is possible to arrange the fuel pressure sensor 20 at an optional location in the fuel passage. The ECU 30 calculates the fuel density ρ of the fuel on the basis of the speed v of the fuel pressure wave. That is, it is possible for the ECU 30 to calculate the fuel density ρ of the fuel on the basis of a physical relationship between the speed v of the fuel pressure wave and the fuel density ρ of the fuel.

The ECU 30 calculates the kinematic viscosity ν of the fuel on the basis of the calculated fuel density ρ of the fuel and the calculated cetane number CN. That is, it can be understood that there is a correlation between the fuel density ρ of the fuel and the cetane number CN of the fuel. Further, according to the experimental results performed by the inventors of the present invention, it can be understood to further increase a degree of the correlation between the fuel density ρ of the fuel and the cetane number CN of the fuel in consideration of the cetane number of the fuel. Accordingly, it is possible to calculate the kinematic viscosity ν of the fuel on the basis of the fuel density ρ of the fuel.

Because the kinematic viscosity ν of the fuel shows the characteristics of fuel as a lubricant, it is possible for the ECU 30 to judge whether or not the fuel properties are correct on the basis of the kinematic viscosity ν of the fuel. Thus, it is possible for the ECU 30 to detect the fuel properties on the basis of the fuel pressure detected by the fuel pressure sensor 20 when the fuel injectors 10 inject fuel. Accordingly, it is thereby possible to correctly and quickly detect the properties of the fuel currently used in the diesel engine with high accuracy.

The fuel injectors 10 inject fuel so that the fuel injection amount Q calculated on the basis of the fuel pressure waveform becomes the predetermined fuel amount Qj. Accordingly, it is possible for the ECU 30 to detect the change amount ΔNE of the engine rotation speed while the fuel injectors 10 inject a correct amount of fuel, It is therefore possible for the ECU 10 to calculate a change amount ΔTq of the torque Tq calculated on the basis of the change amount ΔNE of the engine rotation speed NE, and the cetane number CN of fuel with high accuracy.

The ECU 30 calculates the decreased fuel amount ΔPc of the fuel pressure between a timing before the fuel injection of the fuel injector 10 and a timing after the fuel injection of the fuel injector 10 on the basis of the obtained waveform of the fuel pressure. Further, the ECU 30 calculates an injection amount Q of the fuel by the fuel injector 10 on the basis of the obtained waveform of the fuel pressure. The ECU 30 calculates the fuel density ρ of the fuel on the basis of the calculated speed v of the fuel pressure wave, the calculated decreased fuel amount ΔPc and the calculated fuel injection amount Q, and the volume V of the fuel passage. That is, it is possible for the ECU 30 to calculate the fuel density ρ of the fuel, by using the obtained waveform of the fuel pressure only, on the basis of the physical relationship between the calculated speed v of the fuel pressure wave, the calculated decreased fuel amount ΔPc and the calculated fuel injection amount Q, and the volume V of the fuel passage.

That is, the ECU 30 as the fuel property judgment device according to the exemplary embodiment easily calculates the kinematic viscosity ν of the fuel on the basis of the fuel density ρ and the cetane number CN of the fuel.

The ECU 30 calculates the speed v of the fuel pressure wave by dividing the length 2L, which is twice of the fuel passage length L, by the period T of the pulsation of the waveform of the fuel pressure. Accordingly, it is possible for the ECU 30 to easily calculate the speed v of the fuel pressure wave on the basis of the period T of the pulsation of the waveform of the fuel pressure and the fuel passage length L.

The characteristics of the fuel injection by the fuel injector 10 are changed on the basis of the kinematic viscosity ν. It is therefore possible for the ECU 30 to adjust the fuel injection state of the fuel injector 10 on the basis of the calculated kinematic viscosity ν of the fuel. This makes it possible for the fuel injectors 10 to inject the fuel according to the fuel properties.

It is possible to have the following modifications of the fuel property judgment device according to the exemplary embodiment. It is possible for the ECU 30 to calculate the period T of the pulsation of the waveform of the fuel pressure by performing the frequency analysis of the obtained waveform of the fuel pressure.

Further, it is possible to use the following method in order to calculate the cetane number CN of the fuel.

An additional pressure sensor (internal pressure sensor) capable of detecting an internal pressure of fuel in the cylinder of the diesel engine is mounted on the diesel engine, the ECU 30 receives a detection signal transmitted from the internal pressure sensor and calculates a timing of fuel ignition on the basis of the internal pressure of the cylinder.

The ECU 30 calculates the cetane number of the fuel on the basis of the calculated ignition timing on the basis of a relationship between the ignition timings and cetane numbers, which has been determined by various experiments. Although there are other methods of calculating a cetane number of fuel, the explanation of them is omitted here.

It is also possible to calculate a fuel density ρ of fuel by the following equation: $\rho = K/v^2$.

That is, it is possible for the ECU 30 to calculate the fuel density ρ of fuel on the basis of a volume elasticity K of fuel and the speed v of the fuel pressure wave. It is possible to obtain a volume elasticity K of fuel in advance by experiments, etc. Further, it is possible to calculate the volume elasticity K of fuel by the following equation: $\Delta Pc = K \times Q/V$. That is, it is possible to calculate the volume elasticity K of fuel on the basis of the decreased fuel amount ΔPc of the fuel pressure, the fuel injection amount Q and the volume V of the fuel passage. As previously described, the volume V of the fuel passage is a total sum of the volume of the fuel pipe 42b and the volume of the high pressure passage 11a. It is also possible for the ECU 30 to adjust a supply amount of the fuel supplied from the fuel pump 41 on the basis of the calculated volume elasticity K of the fuel.

As previously described, there is a strong correlation between the fuel density ρ of fuel, the kinematic viscosity v of fuel, and the cetane number of fuel. It is accordingly possible to judge the fuel properties on the basis of the calculated fuel density ρ of fuel and the calculated cetane number CN of fuel.

It is possible to prepare in advance the straight lines (in the graphs shown in FIG. 5 and FIG. 6, for example) representing the correlation between fuel density ρ and kinematic viscosity v of all types of fuel. The ECU 30 calculates the fuel density ρ, and the kinematic viscosity v on the basis of the calculated fuel density ρ on the basis of these straight lines. The ECU 30 adjusts the calculated kinematic viscosity v on the basis of the calculated cetane number CN. In more detail, the ECU 30 decreases the kinematic viscosity v when the cetane number decreases, and on the other hand, the ECU 30 increases the kinematic viscosity v when the cetane number increases. That is, when the cetane number of fuel is a low value, the ECU 30 decreases the calculated kinematic viscosity v of the fuel, as compared with the kinematic viscosity v of fuel when the cetane number of the fuel is a high value. This makes it possible for the ECU 30 as the fuel property judgment device according to the exemplary embodiment to calculate the kinematic viscosity v of fuel with high accuracy.

There is a possible judgment that fuel has good properties when the kinematic viscosity v of the fuel is higher than a judgment value vr. In this case, the kinematic viscosity v of the fuel becomes larger than the judgment value vr so long as the fuel density ρ of the fuel is larger than a judgment value ρr. Accordingly, when the fuel density ρ of fuel calculated by the process in step S12 to step S16 is more than the judgment value pr (as the predetermined density), it is possible for the ECU 30 to judge that the fuel has correct fuel properties without performing the process in step S21 to step S24.

Similarly, when the cetane number CN of fuel is more than a judgment value CNr, the kinematic viscosity v of the fuel becomes more than the judgment value vr. Accordingly, when the cetane number CN of fuel calculated by the process in step S12 to step S16 is higher than the judgment value CNr, it is possible for the ECU 30 to judge that the fuel has correct fuel properties without performing the process in step S12 to step S16.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A fuel property judgment device for use in a fuel injection system, the fuel injection system comprising a pressure accumulation chamber configured to store high pressure fuel, one or more fuel injectors having a fuel injection hole through which the fuel is injected, a fuel passage through which the fuel is supplied from the pressure accumulation chamber to the fuel injection hole, and a fuel pressure sensor configured to detect a fuel pressure of the fuel in the fuel passage, the fuel property judgment device comprising:

an engine control system including a central processing unit and computer readable memory, the engine control system being configured to at least provide:

a fuel pressure waveform acquisition that acquires a waveform of a fuel pressure which represents a change of a fuel pressure of the fuel on the basis of the fuel pressure detected by the fuel pressure sensor when the fuel injector injects the fuel;

a fuel pressure wave speed calculation that calculates a speed of a fuel pressure wave which forms the waveform of the fuel pressure on the basis of a period of a pulsation of the waveform of the fuel pressure obtained by the fuel pressure waveform acquisition and a fuel passage length;

a fuel density calculation that calculates a density of the fuel on the basis of the speed of a fuel pressure wave calculated by the fuel pressure wave speed calculation;

a fuel cetane number calculation that calculates a cetane number of the fuel;

a fuel kinematic viscosity calculation that calculates a kinematic viscosity of the fuel on the basis of the density of the fuel calculated by the fuel density calculation and the cetane number of the fuel calculated by the fuel cetane number calculation; and a judgment that judges a state of fuel properties of the fuel on the basis of the kinematic viscosity of the fuel calculated by the fuel kinematic viscosity calculation.

2. A fuel property judgment device for use in a fuel injection system, the fuel injection system comprising a pressure accumulation chamber configured to store high pressure fuel, one or more fuel injectors having a fuel injection hole through which the fuel is injected, a fuel passage through which the fuel is supplied from the pressure accumulation chamber to the fuel injection hole, and a fuel pressure sensor configured to detect a fuel pressure of the fuel in the fuel passage, the fuel property judgment device comprising:

an engine control system including a central processing unit and computer readable memory, the engine control system being configured to at least provide:

a fuel pressure waveform acquisition that acquires a waveform of a fuel pressure which represents a change of a fuel pressure of the fuel on the basis of the fuel pressure detected by the fuel pressure sensor when the fuel injector injects the fuel;

a fuel pressure wave speed calculation that calculates a speed of a fuel pressure wave which forms the waveform of the fuel pressure on the basis of a period of a pulsation of the waveform of the fuel pressure obtained by the fuel pressure waveform acquisition and a fuel passage length;

a fuel density calculation that calculates a density of the fuel on the basis of the speed of a fuel pressure wave calculated by the fuel pressure wave speed calculation;

a fuel cetane number calculation that calculates a cetane number of the fuel; and a judgment that judges a state of fuel properties of the fuel on the basis of the density of the fuel calculated by the fuel density calculation and the cetane number of the fuel calculated by the fuel cetane number calculation.

3. The fuel property judgment device according to claim 1, wherein the engine control system is configured to further provide:

a fuel injection amount calculation that calculates an injection amount of the fuel to be injected by the fuel injector on the basis of the waveform of the fuel pressure acquired by the fuel pressure waveform acquisition, wherein an internal combustion engine, on which the fuel injection system is mounted, is equipped with an engine rotation speed sensor configured to detect an engine rotation speed of the internal combustion engine, and wherein the fuel cetane number calculation calculates a cetane number of the fuel on the basis of a change amount of the engine rotation speed detected by the engine rotation speed sensor when the fuel injector injects the fuel so that the fuel injection amount calculated by the fuel injection amount calculation becomes equal to a predetermined amount.

4. The fuel property judgment device according to claim 1, wherein the engine control system is configured to further provide:

a decrease amount calculation that calculates a decrease amount of the fuel pressure between a timing before the fuel injection of the fuel injector and a timing after the fuel injection of the fuel injector; and a fuel injection amount calculation that calculates an injection amount of the fuel of the fuel injector on the basis of the waveform of the fuel pressure acquired by the fuel pressure waveform acquisition, wherein the fuel density calculation calculates the density of the fuel on the basis of the speed of the fuel pressure wave calculated by the fuel pressure wave speed calculation, the decrease amount of the fuel calculated by the decrease amount calculation, the fuel injection amount calculated by the fuel injection amount calculation, and a volume of the fuel passage.

5. The fuel property judgment device according to claim 1, wherein the fuel kinematic viscosity calculation calculates the kinematic viscosity of the fuel on the basis of the fuel density calculated by the fuel density calculation by using a correlation obtained in advance between the density of the fuel, the kinematic viscosity of the fuel and the cetane number of the fuel.

6. The fuel property judgment device according to claim 1, wherein the fuel kinematic viscosity calculation calculates a kinematic viscosity of the fuel on the basis of the fuel density calculated by the fuel density calculation by using a correlation obtained in advance between the density of the fuel and the kinematic viscosity of the fuel, and the fuel kinematic viscosity calculation adjusts the kinematic viscosity of the fuel on the basis of the cetane number of the fuel calculated by the fuel cetane number calculation.

7. The fuel property judgment device according to claim 1, wherein the fuel pressure wave speed calculation calculates a speed of the fuel pressure wave by dividing a length which is twice of the fuel passage length by the period of the pulsation of the waveform of the fuel pressure.

8. The fuel property judgment device according to claim 1, wherein the engine control system is configured to further provide a control that controls the fuel injection of the fuel injector on the basis of the kinematic viscosity of the fuel calculated by the fuel kinematic viscosity calculation.

9. The fuel property judgment device according to claim 1, wherein when the fuel density calculated by the fuel density calculation is higher than a predetermined density, the judgment judges that the fuel has correct properties, without calculating the cetane number of the fuel by the fuel cetane number calculation.

10. The fuel property judgment device according to claim 1, wherein when the cetane number of the fuel calculated by the fuel cetane number calculation is higher than a predetermined cetane number, the judgment judges that the fuel has correct properties without calculating the fuel density by the fuel density calculation.

11. A method of judging fuel properties to be used in a fuel injection system comprising: a pressure accumulation chamber configured to store high pressure fuel; one or more fuel injectors having a fuel injection hole through which the fuel is injected; a fuel passage through which the fuel is supplied from the pressure accumulation chamber to the fuel injection hole; and a fuel pressure sensor configured to detect a fuel pressure of the fuel in the fuel passage, the method being performed by a fuel property judgment device comprising an engine control system including a central processing unit (CPU) and computer readable memory, and the method comprising:

acquiring a waveform of a fuel pressure which representing a change of a fuel pressure of the fuel on the basis of the fuel pressure detected when the fuel injector injects the fuel;

calculating a speed of a fuel pressure wave which forms the waveform of the fuel pressure on the basis of a period of a pulsation of the waveform of the fuel pressure and a fuel passage length;

calculating a density of the fuel on the basis of the speed of the calculated fuel pressure wave;

calculating a cetane number of the fuel;

calculating a kinematic viscosity of the fuel on the basis of the calculated density of the fuel and the calculated cetane number of the fuel; and judging a state of fuel properties of the fuel on the basis of the calculated kinematic viscosity of the fuel.

12. The fuel property judgment device according to claim 2, wherein the engine control system is configured to further provide:

a fuel injection amount that calculates an injection amount of the fuel to be injected by the fuel injector on the basis of the waveform of the fuel pressure acquired by the fuel pressure waveform acquisition, wherein an internal combustion engine, on which the fuel injection system is mounted, is equipped with an engine rotation speed sensor configured to detect an engine rotation speed of the internal combustion engine, and wherein the fuel cetane number calculation calculates a cetane number of the fuel on the basis of a change amount of the engine rotation speed detected by the engine rotation speed sensor when the fuel injector injects the fuel so that the fuel injection amount calculated by the fuel injection amount calculation becomes equal to a predetermined amount.

13. The fuel property judgment device according to claim 2, wherein the engine control system is configured to further provide:

a decrease amount calculation that calculates a decrease amount of the fuel pressure between a timing before the fuel injection of the fuel injector and a timing after the fuel injection of the fuel injector; and a fuel injection amount calculation that calculates an injection amount of the fuel of the fuel injector on the basis of the waveform of the fuel pressure acquired by the fuel pressure waveform acquisition, wherein the fuel density calculation calculates the density of the fuel on the basis of the speed of the fuel pressure wave calculated by the fuel pressure wave speed calculation, the decrease amount of the fuel calculated by the decrease amount calculation, the fuel injection amount calculated by the fuel injection amount calculation, and a volume of the fuel passage.

14. The fuel property judgment device according to claim 2, wherein the fuel pressure wave speed calculation calculates a speed of the fuel pressure wave by dividing a length which is twice of the fuel passage length by the period of the pulsation of the waveform of the fuel pressure.

15. The fuel property judgment device according to claim 2, wherein when the fuel density calculated by the fuel density calculation is higher than a predetermined density, the judgment judges that the fuel has correct properties, without calculating the cetane number of the fuel by the fuel cetane number calculation.

16. The fuel property judgment device according to claim 2, wherein when the cetane number of the fuel calculated by the fuel cetane number calculation is higher than a predetermined cetane number, the judgment judges that the fuel has correct properties without calculating the fuel density by the fuel density calculation.

* * * * *